United States Patent
Nguyen (10) Patent No.: US 8,880,164 B2
(45) Date of Patent: Nov. 4, 2014

(54) METHOD AND SYSTEM FOR DETERMINING A VARIATION IN A METABOLIC FUNCTION AND MANAGING THE VARIATION ACCORDINGLY

(75) Inventor: Hung Tan Nguyen, Castle Hill (AU)

(73) Assignee: University of Technology, Sydney Ultimo, New South Wales (AU)

( * ) Notice: Subject to any disclaimer, the term of this patent is extended or adjusted under 35 U.S.C. 154(b) by 397 days.

(21) Appl. No.: 13/265,400

(22) PCT Filed: Apr. 20, 2010

(86) PCT No.: PCT/AU2010/000445
§ 371 (c)(1),
(2), (4) Date: Dec. 29, 2011

(87) PCT Pub. No.: WO2010/121301
PCT Pub. Date: Oct. 28, 2010

(65) Prior Publication Data
US 2012/0095359 A1    Apr. 19, 2012

(30) Foreign Application Priority Data

Apr. 20, 2009  (AU) ............... 2009901693

(51) Int. Cl.
*A61B 5/04* (2006.01)
*A61B 5/048* (2006.01)
*A61B 5/00* (2006.01)
*A61F 2/02* (2006.01)
*G06F 19/00* (2011.01)

(52) U.S. Cl.
CPC ............ *A61B 5/048* (2013.01); *A61B 5/4866* (2013.01); *A61F 2/022* (2013.01); *G06F 19/345* (2013.01); *A61B 5/7264* (2013.01); *A61B 5/7267* (2013.01)

USPC .......................................... 600/544

(58) Field of Classification Search
USPC .......................................... 600/544
See application file for complete search history.

(56) References Cited

U.S. PATENT DOCUMENTS

| 6,572,542 B1 | 6/2003 | Houben et al. |
| 2004/0077966 A1* | 4/2004 | Yamaguchi et al. .......... 600/544 |
| 2008/0294031 A1* | 11/2008 | Wilson et al. ................. 600/383 |

FOREIGN PATENT DOCUMENTS

| WO | WO 02/69798 | 9/2002 |
| WO | WO 2006/066577 | 6/2006 |
| WO | WO 2007/144307 | 12/2007 |
| WO | WO 2009/090110 | 7/2009 |

OTHER PUBLICATIONS

International Search Report for PCT/AU2010/000445 mailed Jun. 2, 2010.
Written Opinion of International Searching Authority mailed Jun. 2, 2010.

\* cited by examiner

*Primary Examiner* — Etsub Berhanu (57) ABSTRACT

This invention describes a method for determining an abnormality of metabolic function and/or a variation of metabolic function, the method including the steps of, in a processing system receiving electroencephalography (EEG) signal information (100), analyzing the signal information (110), and determining the abnormality from the analysis (120). It also describes a method for managing the variation accordingly, the method including the steps of, detecting the abnormality (400), applying patient information (410), determining appropriate dose (420), and providing the required dose (430).

21 Claims, 7 Drawing Sheets

METHOD AND SYSTEM FOR DETERMINING A VARIATION IN A METABOLIC FUNCTION AND MANAGING THE VARIATION ACCORDINGLY

This application is the U.S. national phase of International Application No. PCT/AU2010/000445, filed 20 Apr. 2010, which designated the U.S. and claims priority to AU 2009901693, filed 20 Apr. 2009, the entire contents of each of which are hereby incorporated herein by reference.

FIELD OF THE INVENTION

The present invention relates to a method and system for determining a variation in a metabolic function, and in particular, a method and system for determining an abnormality such as the presence of hypoglycaemia in a diabetic patient. According to one particular example, a method and system for managing a metabolic function, and in one example, managing hypoglycaemia is also provided.

DESCRIPTION OF THE BACKGROUND ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Presently, it has become apparent that it is quite difficult to diagnose, monitor, and manage metabolic diseases.

An example of a metabolic disease is diabetes mellitus. In diabetes, sufferers generally have abnormally high blood glucose levels due to a reduced production of insulin (referred to as Type 1 diabetes), or have become resistant to the effects of insulin (referred to as Type 2 diabetes), which is secreted by the pancreas to control blood sugar levels.

Various organs of the body, and in particular, the brain, depend on a continual supply of glucose and are vulnerable to any glucose deprivation. Unable to synthesise or store this primary source of energy, the brain is one of the first organs affected by lowered blood glucose levels. Hypoglycaemia develops when rates of glucose entry into the systemic circulation are reduced relative to glucose uptake by tissues. Hypoglycaemia is usually corrected naturally by the combination of a number of defence mechanisms. Initially, a decrease in insulin secretion in response to declining blood glucose levels occurs. As glucose levels continue to fall, a number of redundant glucose counter-regulatory factors are sequentially activated at specific thresholds to ensure sufficient glucose uptake to the brain and other central nervous system tissue metabolism. These counter-regulatory factors include glucagon, epinephrine, growth hormone, cortisol, and other hormones.

Generally, hypoglycaemia may be defined in a physiological context, as a plasma glucose of <3.9 mmol/l (<3.3 mol/l whole blood). Glycaemic thresholds for activation of the anti-insulin neuro-endocrine counter-regulatory response occurs at plasma glucose values of approximately 3.2 to 3.8 mmol/l. Additionally, antecedent hypoglycaemia has been demonstrated to reduce counter-regulatory responses to subsequent hypoglycaemia.

In patients with Type 1 diabetes undergoing intensive insulin therapy, falling plasma glucose concentrations often do not elicit counter-regulatory responses at normal glycaemic thresholds, allowing glucose levels to drop to dangerously low values. After the first few years of diabetes, the glucagon counter-regulatory response to hypoglycaemia becomes deficient. Additionally, in some cases warning symptoms no longer occur, and the episode may lead to serious complications, such as coma and convulsions. This phenomenon is known as hypoglycaemia unawareness. Studies in patients have demonstrated that as few as two episodes of antecedent hypoglycaemia can blunt responses to subsequent hypoglycaemia.

Symptoms of hypoglycaemia arise from the activation of the autonomous central nervous system (autonomic symptoms) and from reduced cerebral glucose consumption (neuroglycopenic symptoms), some of the latter being potentially life threatening. Nocturnal hypoglycaemia is particularly dangerous because sleep reduces and may obscure autonomic counter-regulatory responses, so that an initially mild episode may become severe. The risk of severe hypoglycaemia is high at night, with at least 50% of all severe episodes occurring during that time.

Even with modest insulin elevations, deficient glucose counter-regulation may also lead to severe hypoglycaemia. Regulation of nocturnal glycaemia is further complicated by the dawn phenomenon. This is a consequence of nocturnal changes in insulin sensitivity following growth hormone secretion: a decrease in insulin requirements approximately between midnight and 5 am, followed by an increase in requirements between 5 am and 8 am.

Thus, there is required a system and/or method for determining an abnormality in metabolic function, which overcomes, at least ameliorates one or more disadvantages of existing arrangements, or provides an alternative to existing arrangements.

SUMMARY OF THE PRESENT INVENTION

According to a first broad form, there is provided herein a method for determining a variation in a metabolic function, the method including the steps of in a processing system: receiving electroencephalography (EEG) signal information; analysing the signal information; and, determining the variation from the analysis.

In one example, the method includes receiving signal information in a continuously moving time window. In another example, the method allows/provides for real-time detection of the abnormality of metabolic function and/or a variation of metabolic function.

According to another example, the method includes receiving the EEG signal information including any one or a combination of: an alpha wave; a theta wave; and, a delta wave.

In a further form, analysing the signal information includes any one or a combination of: determining a shift in a centroid alpha frequency; determining a shift in a centroid theta frequency; determining a shift in a centroid delta frequency; determining a rate of change of the alpha wave frequency; determining a rate of change of the theta wave frequency; and, determining a rate of change in the delta wave frequency.

In one aspect, determining the variation of metabolic function includes determining an indication of the presence of hypoglycaemia.

In yet another example, the method includes providing an indication of hypoglycaemia by receiving information of a slowing of alpha wave activity, an increase in delta wave and theta wave activity of the EEG signal.

According to another aspect, the method further includes determining an average time constant of hypoglycaemic episodes and a natural time constant related to normal sleep patterns, for detecting hypoglycaemia during sleep.

In a further example, the method includes performing a data mining technique on the signal information to determine an abnormality of metabolic function and/or a variation of metabolic function.

In another example, the method includes applying an artificial or optimised Bayesian neural network.

In yet another example, the method includes training data in relation to EEG signals, associated with a particular patient.

According to a further form, the method includes: estimating a patient model based on an EEG response; and, calculating an appropriate medicament dose for managing the variation.

According to another example, the method includes generating a signal to cause an automatic administration of the medicament dose.

With respect to another example, the method includes sounding an alarm when a variation is determined.

In yet another form, the variation is an indication of hypoglycaemia and the appropriate glycogen/glucose dose is calculated.

According to another example, the dose is administered by any one or a combination of: a pump; an oral device; a medicament dispenser; and, an intravenous device.

In a second broad form there is provided herein a system for determining a variation in a metabolic function, the system including a processing system, the processing system being configured to: receive electroencephalography (EEG) signal information; analyse the signal information; and, determine the variation from the analysis.

In one example, the processing system receives EEG signal information from a wireless headset.

According to yet another form, there is provided herein an artificial pancreas for managing hypoglycaemia, the artificial pancreas including: a processing system, the processing system being configured to receive information associated with an onset of hypoglycaemia, in accordance with any of the methods described herein; and, an administration device, the administration being configured to administer an appropriate does of glucose/glycogen to manage hypoglycaemia.

In one particular form, the pancreas is used as an overnight device.

According to another example, the pancreas is at least partially implantable.

It will be appreciated that any of the examples, forms, or aspects described above can be provided individually or in combination.

BRIEF DESCRIPTION OF THE DRAWINGS

An example of the present invention will now be described with reference to the accompanying drawings, in which:—

DETAILED DESCRIPTION INCLUDING BEST MODE

An example of a method/process for determining a variation, such as an abnormality in a metabolic function will now be described with reference to FIG. 1.

Figure 1:
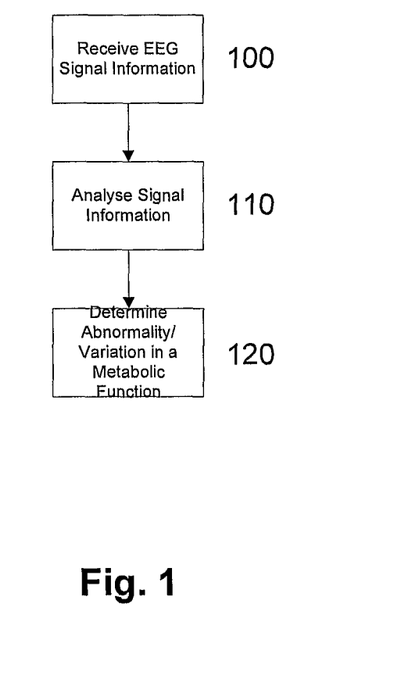
FIG. 1 is a flow diagram of an example method/process that can be utilised to embody or give effect to a particular embodiment.

In particular, FIG. 1 shows at step 100, receiving electroencephalography (EEG) signal information, analysing the signal information at step 110, and determining the abnormality from the analysis at step 120.

The process of FIG. 1 can be performed using any type of processing system, an example of which will now be described with reference to FIG. 2.

Figure 2:
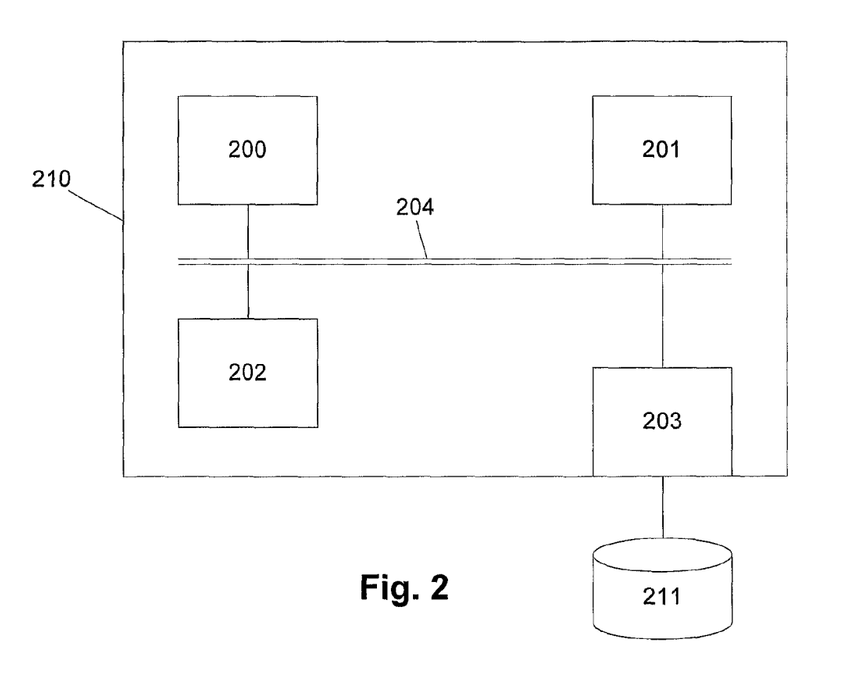
FIG. 2 is a functional block diagram of an example processing system that can be utilised to embody or give effect to a particular embodiment.

FIG. 2 shows a processing system 210, which can be optionally coupled to one or more databases 211. In this particular example, the processing system 210 includes processor 200, a memory 201, an input/output (I/O) device 202, such as a keyboard, and display, and an external interface 203, coupled together via a bus 204 as shown. It will be appreciated by persons skilled in the art that, any form of suitable processing system 210 may be used.

Accordingly, it will be appreciated that the processing system 210 may be formed from any suitable processing system, such as a suitably programmed PC, microprocessor, Internet or networked terminal, lap-top, hand-held PC, or the like.

Figure 3:
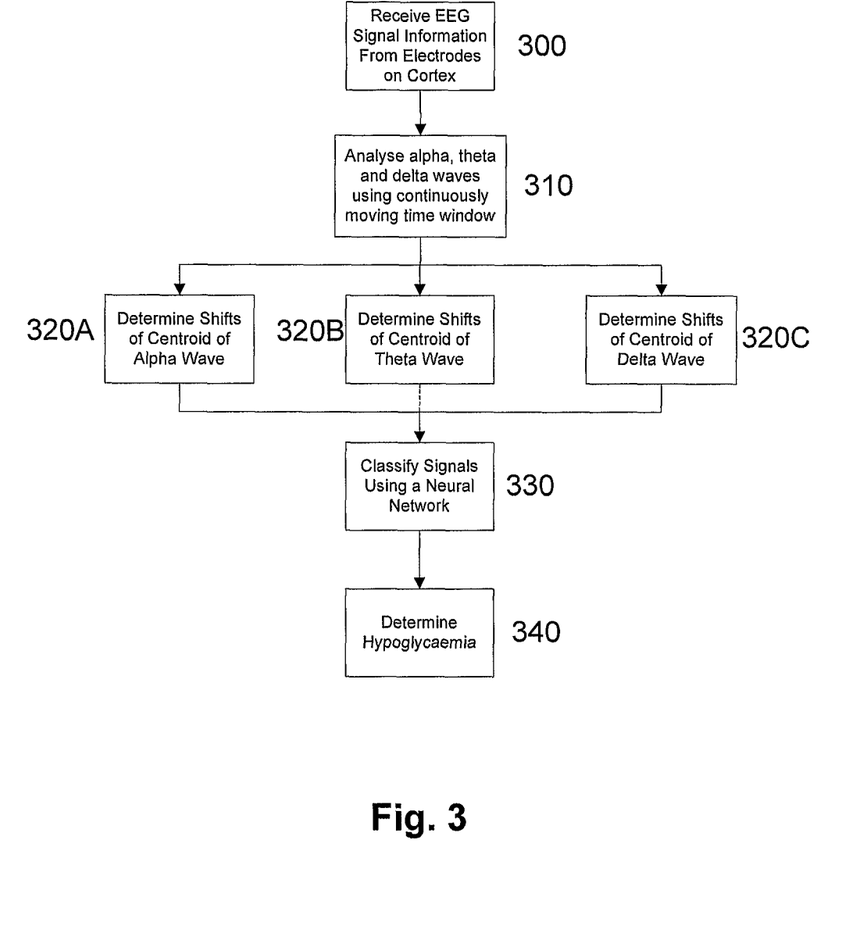
FIG. 3 is another flow diagram of an example method/process that can be utilised to embody or give effect to a particular embodiment.

FIG. 3 shows a further example of a method for determining a variation such as an abnormality in a metabolic function.

In this example, at step 300 EEG signal information is received from one or more electrodes placed on an area of the head. Thus, the system may form part of a wireless headset which is placed around a patient's head. Examples of electrode placement are further described below. In one particular example, the EEG signal is received from the occipital and/or parietal cortex (O1, O2, P3, or P4).

At step 310, the method can include analysing the received signal, and in particular, receiving signal information in a continuously moving time window to allow for real-time detection of the abnormality, where the signal information can represent, be associated with, or include data in relation to an alpha wave, a theta wave, a delta wave, or the like of the EEG signal.

At steps 320A to 320C it can be determined whether there is a shift in the centroid alpha frequency, centroid theta frequency, and/or centroid delta frequency. In particular, the shifting can include any one or a combination of slowing alpha wave activity, quickening theta wave activity, and increasing delta wave activity. The presence of an abnormality of a metabolic condition, such as that of hypoglycaemia can be determined and/or monitored as a result of any shifting, as seen at step 340.

Notably, and as discussed below, data mining, such as a neural network or the like, may only use the shifting in one, two or all three waves to make a decision and/or determine abnormal metabolic function. For example, if a very noisy delta wave is received, the information associated with this wave may be removed before feeding other EEG associated information and various features from different waves into the neural network. However, the delta wave information may still be recorded and kept in case it is needed for further analysis.

Thus, it may be possible that an appropriate shifting in the centroid of the alpha waves would be adequate for the detection of hypoglycaemia.

Additionally, it will further be appreciated that other EEG wave information such as the shift in beta waves may also be used.

According to yet a further example, various features from the three waves can be fed directly to the neural network at the same time, and in one particular example, this can include the alpha and theta waves. These features can include the shift in centroid of the waves and their associated time constants (how they are shifting against time), and can also include their rates of change.

As described, and as, shown at step 330, the process can also include performing a data mining technique in order to determine the abnormality. In this particular example, the method includes classifying the signals by using/applying an artificial neural network, and further an optimised Bayesian neural network. Examples of the application of a neural network is further discussed below, although it will be appreciated by persons skilled in the art that any form of appropriate data mining technique may be used.

Figure 4:
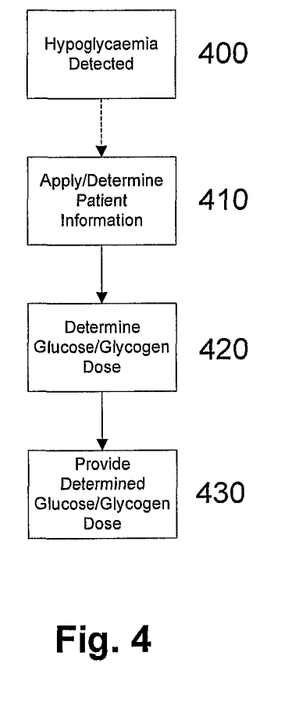
FIG. 4 is another flow diagram of an example method/process that can be utilised to embody or give effect to a particular embodiment.

FIG. 4 shows a further example of a process which can be implemented once an abnormality has been detected.

In this particular example, hypoglycaemia is detected at step 400. At step 410, patient information is used/applied, that is a patient model may be estimated based on the determined abnormality and patient information. Notably, in this example, step 410 is an optional step and the patient information may not particular be required.

At step 420, an appropriate medicament dose can be calculated for managing the abnormality, and as result, at step 430 the calculated/determined glucose/glycogen dose may be provided (to manage the hypoglycaemia). This can occur by generating a signal to cause the administration of the medicament dotes.

Thus, the generated signal can cause a dose to be automatically administered via a glucose/glycogen pump, an oral device, and/or an intravenous device, or the like.

The process of FIG. 4 can be implemented to provide an overall system of detecting and managing a condition such as hypoglycaemia, and in particular, and be implemented as an artificial pancreas, further examples of which are described below.

According to yet a further example, the process of FIG. 4 can include administering a basic glucose does and determining an appropriate dose after receiving feedback from the patient.

Hence, the system and method described herein can provide a real-time non-invasive and continuous hypoglycaemia monitor that employs EEG signals only. It will be appreciated that with the described system and method, it may be possible to detect hypoglycaemia early, using only selected physiological parameters associated with the development of hypoglycaemia. These physiological parameters can include EEG changes related to the slowing of a waves, the quickening of theta (θ) waves and the appearance of coarse delta (δ) waves. Real-time analysis of the effectiveness of these EEG changes and optimal Bayesian neural-network modelling can provide a basis for the early detection of hypoglycaemia in Type 1 diabetes patients, including those with hypoglycaemia unawareness.

Notably, an advantage of hypoglycaemia detection using EEG, which can be provided is that neuroglycopaenic measures are usually not reduced in patients with hypoglycaemia unawareness or during states of diminished autonomic responses such as sleep. It would be possible to allow the system to learn as it gains experience about hypoglycaemia. Accordingly, the continuous detection of natural occurrence of nocturnal hypoglycaemia can be focused on due to the risk of severe hypoglycaemia is high at night.

It will also be appreciated that the system can form a part of a monitoring system for monitoring patients by their carers, or the like. Furthermore, the method and system described herein can focus on the detection of neuroglycopenic symptoms of hypoglycaemia. Additionally, although hypoglycaemia has been used herein as an example of a metabolic function which can be determined, managed, or the like, it will also be appreciated that the presently described system/method may be applied to other bodily functions.

Further Examples

According to one particular example, the presently described system and method can be used to identify hypoglycaemic episodes continuously and non-invasively at night using EEG signals. Furthermore, the system can be used to normalise blood glucose levels (BGL) automatically in Type 1 patients with diabetes or insulin-dependent Type 2 patients with diabetes.

A first feature of this example, is that the detection of hypoglycaemic episodes (eg. BGL≤3.3 mmol/L) can be detected with sufficient speed and accuracy by continuous and non-invasive means using only one or two EEG channels with the main physiological parameters being the centroid alpha frequency, the centroid theta frequency and their rates of change.

A second feature is the use of a Bayesian neural network for the detection of hypoglycaemia, which has the ability to adapt to an individual patient.

Additionally, a third feature which can be implemented is the detection of hypoglycaemic episodes, which can trigger an intelligent closed-loop control algorithm. This action can activate appropriate glucose/glucagon dose automatically through a glucose pump to normalise blood glucose levels in patients. It will be appreciated that were it not for the potentially devastating effect of hypoglycaemia on the brain, the glycaemic management of diabetes would have been a relatively simple process. Thus, development of an overnight artificial pancreas can offer substantial improvements in overall glucose control and can allow for normoglycaemia at the start of the day.

Each of the features described above are described in more detail below.

Detection of Hypoglycaemia

In this particular example, the earliest symptom for hypoglycaemia can be found by the use of EEG. EEG normally consists of alpha waves (α: 8-13 Hz) and beta waves (β: 13-2 Hz). In addition, theta waves (θ: 4-8 Hz), which can be a very minor component of the EEG, and delta waves (δ: 1-4 Hz), which can be minimal in a normal awake state, can also be used. As the blood glucose levels progressively drop in hypoglycaemia to the range of 1-2 mmol/l, θ waves increase and coarse δ waves appear. These are accompanied by clinical stupor or drowsiness. In addition, there is a slowing of α waves, which corresponds to a decrease of vigilance. This characteristic has also proved to be the most sensitive for hypoglycaemia unawareness.

EEG patterns correlate with cerebral metabolic rate for glucose and cerebral energy state as assessed by energy charge potentials. A decrease in the cerebral metabolic rate for glucose is associated with a slowing of the EEG pattern; an increase in slow waves precedes convulsive, polyspike activity and an isoelectric EEG. Subsequent coma or isoelectricity has always been associated with the sudden disintegration of energy balance. Since an increase in slow waves precedes severe cerebral energy derangement while plateauing the level of available energy charge potentials, it is a protective phenomenon that delays eventual energy failure in hypoglycaemia. It has also been found that during wakefulness, pronounced increase in delta and theta relative power preceded severe cognitive impairment by approximately 20 minutes.

Thus, according to one example, there is provided herein a method of detecting hypoglycaemia continuously and non-invasively using EEG signals from one or two channels only. The main EEG inputs/sensors may be positioned on the visual cortex (such as O1 or O2), parietal cortex (such as P3 or P4), and/or parietal-occipital area (such as PO3 or PO4), as described in the standard International 10-20 System of EEG electrode placement. Notably, the reference input of this EEG channel may be located on one of the earlobes (A1 or A2) or any of the other main EEG sites.

Accordingly, there is provided herein a method of developing a non-invasive and continuous model for detecting hypoglycaemia, using EEG changes related to the slowing of alpha wave activity and the increase in theta and delta wave activity. In particular, hypoglycaemia is correlated significantly with the physiological parameters associated with EEG signals (such as centroid alpha frequency, centroid theta frequency and other physiological parameters derived from EEG).

Application of Artificial Neural Networks

Hypoglycaemia can be detected using EEG and an advanced optimal Bayesian neural-network algorithm. In this particular example, the neural network has a multilayer feed-forward neural network structure with one input layer, one hidden layer, and one output layer.

The training of a Bayesian neural network can adjust weight decay parameters automatically to optimal values for the best generalisation by estimating the evidence for each model and no separate validation set is required. In evidence framework, the Gaussian assumptions are used to approximate the posterior distribution of weights and biases. The regularisation is undertaken to prevent any weights becoming excessively large, which can cause poor generalisation. In particular, for multi-layer perception neural network classifiers with G different groups of weights and biases, the "weight decay" is added to the data error function $E_D$ in order to obtain the objective function in the form:

$$S = E_D + \sum_{g=1}^{G} \xi_g E_{W_g}, \quad (1)$$

$$E_D = -\sum_{n=1}^{N} \{t^{(n)} \ln z^{(n)} + (1 - t^{(n)}) \ln(1 - z^{(n)})\},$$

$$E_{W_g} = \frac{1}{2} \|w_g\|^2$$

where $E_D$ is the "cross-entropy" data error function and $E_{W_g}$ (g=1, ..., G) are weight functions corresponding to weight and bias groups, $\xi_g$ are "non-negative" scalars, sometimes called hyperparameters for controlling the distributions of weights and biases in different groups and $w_g$ is the vector of weights or biases in the g th group. The evidence of a two-layer network $X_i$ with M hidden nodes is given by:

$$\log Ev(X_i) = -E_D(w) + \ln Occ(w) + \sum_{g=1}^{G} \ln Occ(\xi_g) \quad (2)$$

$$\ln Occ(w) = -\sum_{g=1}^{G} \xi_g^{MP} E_{W_g}^{MP} + \sum_{g=1}^{G} \frac{W_g}{2} \ln \xi_g - \frac{1}{2} \ln|A| + \ln M! + M \ln 2, \quad (3)$$

$$\ln Occ(\xi_g) = \frac{1}{2} \ln\left(\frac{4\pi}{\gamma_g^{MP}}\right) + K$$

where $W_g$ is the number of weights and biases in the g th group and K is a constant. The best network can then be selected with the highest log evidence.

Accordingly, detection of hypoglycaemia can be provided by using EEG signals only. In this particular example, the main parameters used for the detection of hypoglycaemia are derived from $\alpha$, $\theta$, $\delta$ activity from the EEG, and in particular their rates of change. Other important parameters are the time constants associated with these physiological responses. Notably, rates of changes and the time constants inherent in physiological responses are important factors that can be used to reject false detection.

These results were obtained by the following experiment:

Six T1DM adolescents (between the ages of 12 and 18 years) volunteered, with consent from their parents or guardians, for the 10-hour pilot overnight hypoglycaemia monitoring study. Each study consisted of five phases approximately: baseline (1 hr), euglycemia (3 hrs), ramp (1 hr), hypoglycemia (1.5 hrs) and recovery (4.5 hrs).

An EEG system was used to measure the EEG signals, while the actual blood glucose (BG) levels were collected as reference, using Yellow Spring Instruments (as shown in FIG. 9). The HbA1c of the children included a range from 6.5% to 8.9%. In this group of children, severe hypoglycaemia occurred at a rate of 20 episodes per 100 patient years. All experienced occasional mild hypoglycaemia, as is usual during the course of treatment in adolescents with type 1 diabetes. The children's sleep state was monitored and it was discovered that with dim lighting and with experienced nursing and medical staff, arousal or activation was not a complicating factor. During these protocols, the quality of sleep was examined, and it was concluded that it was not impaired by the performance of these clamp studies. Notably, hypoglycaemia occurs frequently at night in adolescents and adults with Type 1 diabetes and that it is unusual for this hypoglycaemia to result in arousal and awakening. If subjects awaken, however, this would be documented.

An optimal neural network algorithm was developed to detect nocturnal mild hypoglycemic episodes (BG<=3.3 mmol/l or 60 md/gl, whole blood). Useful information was limited to a five-hour window from the start of the euglycemia phase to a part of the recovery phase. Associated with the above pilot clinical study, under hypoglycaemic conditions, their centroid alpha frequency reduced significantly (9.908±0.385 vs. 9.656±0.361, P<0.0001) and their centroid theta frequency increased significantly (5.360±0.210 vs. 5.443±0.199, P<0.02). On the other hand, their centroid gamma frequency increased slightly, but not significantly (17.900±0.672 vs. 18.027±0.573, P=0.232). In addition, the power levels associated with the alpha, theta and gamma waves did not change significantly.

The overall dataset was organised into a training set (three cases) and a test set (three cases) randomly selected. Networks with different initial conditions were trained using the quasi-Newton training algorithm. The evidence framework for Bayesian inference was applied to the training set and it was discovered that the feed forward neural-network architecture with 5 hidden nodes yielded the highest evidence. Using a neural network with 5 hidden nodes (optimal) and only physiological parameters including centroid alpha and theta frequencies, the estimated BG profiles produced a significant correlation against measured values. From the optimal neural network which was derived from the training set with the highest log evidence, estimated blood glucose profiles were produced for the test set. Although the monitor is designed to detect hypoglycaemia rather than blood glucose levels, from the pilot data, the Bayesian neural network showed a significant correlation between estimated and measured blood glucose levels for the test set (r=−0.321, P=0.004<0.005). In addition, the predicted hypoglycemia classifications in the test set were found to be correlated significantly to the actual hypoglycemic episodes (r=0.274, P=0.0147<0.02). From the optimal neural network which was derived from the training set, the sensitivity (true positive) value and the specificity (true negative) for the detection of hypoglycemia in the test set are 78% and 55% respectively. It is difficult to estimate the final accuracy of the optimal neural network algorithm at this stage; however, from the preliminary data, a sensitivity greater than 0.85 and specificity of around 0.85 may be achieved.

Notably, during sleep, the EEG has characteristic changes between different sleep stages and is dominated to a greater extent by slower rhythms. In addition, the amount of slow-wave activity changes during the course of a night's sleep. Thus, a number of methods have been developed to minimise these effects. Firstly, through training, the Bayesian neural-network algorithm has the ability to generalise and recognise the characteristics of hypoglycaemic episodes against excursions of sleep stages. Secondly, the adaptive neural-network algorithm can be designed to adapt to a specific group of patients or an individual patient. Thirdly, the natural dynamics (average time constant) of hypoglycaemic episodes and the natural time constant related to normal excursions of sleep stages can be detected and used for positive identification of hypoglycaemia.

Artificial Pancreas

Figure 5:
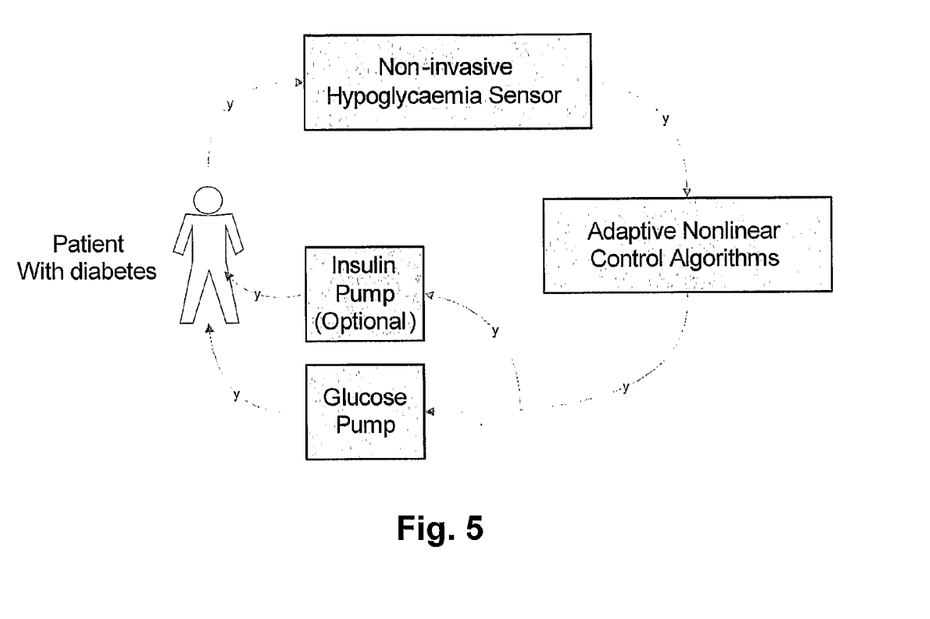
FIG. 5 is a functional block diagram of an example of an artificial pancreas system.

An example of an artificial pancreas is shown in FIG. 5.

In this example, the artificial pancreas includes a non-invasive hypoglycaemia sensor as described herein. The control algorithms are nonlinear and adaptive, and are able to produce the required dose for the glucose/glycogen pump or the glucose dispenser to normalise the blood glucose levels in the patient.

In this particular example, the main priority of the overnight artificial pancreas is to guard against hypoglycaemia automatically. Blood glucose levels in patients at night are in general decreasing continuously. Therefore, the use of insulin pump is only optional (where it can be used to keep the patient's blood glucose levels within certain bounds if required). It is noted that the glucose pump which can be used to inject glucose or glucagon is safer to use than an insulin pump at night.

For calculating the optimal doses of glucose pump/dispenser and also the insulin pump (optional), the minimal model method was used. The minimal model equations may be described by the following equations:

$$\frac{dG(t)}{dt} = -[p_1 + X(t)]G(t) + p_1 G_b$$

-continued $$\frac{dX(t)}{dt} = -p_2 X(t) + p_3 [I(t) - I_b]$$

where t is time, G(t) and I(t) are plasma glucose and insulin concentrations, X(t) is insulin effect, $G_b$ and $I_b$ are basal glucose and insulin concentrations. Insulin sensitivity and glucose effectiveness can be calculated from $$S_I = \frac{p_3}{p_2} \text{ and } S_G = p_1.$$

Denoting a state vector, input and output as x, u and y respectively, a non-linear representation for the minimal model can be found as $$\dot{x} = Ax + Bu$$
$$y = Cx$$

where $$x = \begin{bmatrix} G \\ X \end{bmatrix}, u = \begin{bmatrix} G_i - G_b \\ I - I_b \end{bmatrix}, A = \begin{bmatrix} -p_1 & -G \\ 0 & -p_2 \end{bmatrix}, B = \begin{bmatrix} 0 \\ p_3 \end{bmatrix},$$
$$C = \begin{bmatrix} 1 & 0 \end{bmatrix}$$

The adaptive predictor-observer for this system can be described by:

$$\dot{\hat{x}} = A\hat{x} + Bu + K_o(y - C\hat{x})$$

where $\hat{x}$ is the estimated state vector and $K_o$ is the observer gain vector.

The controller can be found from:

$$u = -K_c \hat{x}$$

where $K_c$ is the controller gain.

This technique can be used for the effective estimation of blood glucose levels in real-time throughout the night. This information can then be used by the controller algorithm in order to calculate and provide appropriate doses for the glucose pump/dispenser and the optional insulin pump (as described below). It is also possible to develop a Bayesian neural network estimator and controller using the above Bayesian framework.

Notably, although FIG. 5 shows an example of a glucose pump or dispenser being used to dispense the required dose of glucose/glycogen, it will be appreciated that many different systems of glucose/insulin delivery can be used. This can include oral or intravenous delivery systems, as well as other types of devices such as patches placed on the skin, or mouth guards which the patient can wear at night, or the like.

It will further be appreciated that the system described can be particularly useful in night time monitoring of hypoglycaemia. That is, a patient can be assisted to manage his/her condition whilst asleep, which can improve the patient's quality of life, as well as aiding in the detection of hypoglycaemia, which can have potentially fatal consequences.

An Overall System Example

Figure 6:
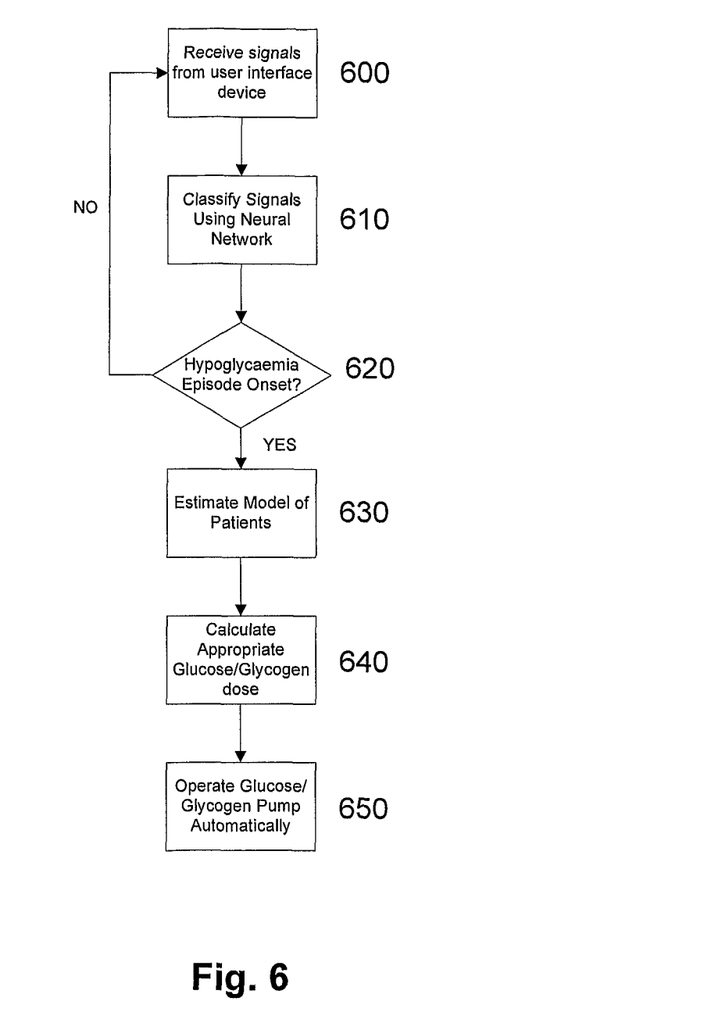
FIG. 6 is another flow diagram of an example method/process that can be utilised to embody or give effect to a particular embodiment.
Figure 7:
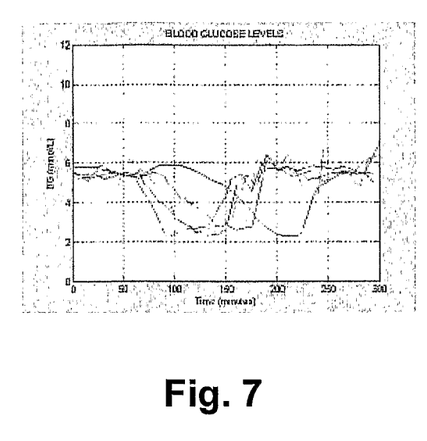
FIG. 7 is a graphical representation of an example of blood glucose profiles.

As shown in FIG. 6, the present invention can provide a method of regulating a patient's metabolic responses overnight continuously including the steps of receiving signals from a user interface device at step 600, classifying the received signals using a neural network with an optimal number of hidden nodes based on the highest level of Bayesian evidence at step 610, classifying onsets of hypoglycaemic episodes at step 620 (with the process returning to step 600 if it is determined that hypoglycaemia was not determined, estimating the model of the patients at step 630, calculating an appropriate glucose or glucagon dose using an intelligent algorithm at step 640, and operate the glucose/glucagon pump automatically at step 650.

Notably, a wireless EEG system can be used to detect the EEG signals and subsequently transmit the signals to receiver for processing. In this example system, the system includes a Tx transmitter head set module and a Rx transceiver module. In the transmitter module, there are two differential EEG channels, a PIC micro-controller and a 2.4 GHz transceiver with a telemetry range of 10 m. The Rx transceiver module can include a 2.4 GHz transceiver for two channels, a PIC micro-controller and USB communication to a PC. The USB receiver uses a virtual COM port for transfer to a tablet (Toshiba M750, Intel Core 2 Duo, 4 GB, 160 GB hard drive) with the baud rate fixed at 115,200 bps. Notably, a small embedded microcontroller system can be developed to be used in place of the Toshiba tablet which can be used to classify intended commands accurately in real-time.

Accordingly, there has been provided herein, according to one particular example, an effective overnight artificial pancreas.

It will be appreciated that the system described can provide numerous advantages, according to one example, the system described herein can operate effectively in substantially real-time without significant time delay as EEG signals provide the earliest evidence for hypoglycaemia.

According to another example, an advantage of hypoglycaemia detection using EEG can be that neuroglycopaenic measures are not reduced in patients with hypoglycaemia unawareness or during states of diminished autonomic responses such as sleep. Further advantages which can be provided are described below.

It will also be appreciated by persons skilled in the art that the device described herein is not limited to the monitoring, regulating and/or managing of hypoglycaemia, and the device described can be used in respect of any metabolic condition or variation.

Notably, the device described herein can also be formed such that it is a part of an at least partially implantable device such as an implantable pancreas, or an external device, an overnight device, or the like.

Example Advantages of the System and Method Described Herein

According to one example, it will be appreciated that hypoglycaemia or low blood glucose is a common and serious side effect of insulin therapy in patients with diabetes. Thus, there is provided herein an alarm that can warn patients of a fall in blood glucose and allow them to prevent a hypoglycaemic episode. Accordingly, the method and system provided herein can use the responses of the body to a fall in glucose to detect the early changes that occur as hypoglycaemia develops. By carefully measuring physiological responses such as EEG (brain wave monitor) and analysing these, hypoglycaemia can be detected non-invasively and continuously. Furthermore, the diagnostic resources of an advanced neural-network algorithm is capable of adapting to each individual patient, which can allow for the development of an innovative and effective monitor that, in turn, promotes improved diabetes control and quality of life for the patient with insulin treated diabetes.

Additionally, it will be appreciated that during sleep, the EEG has characteristic changes between different sleep stages and is dominated to a greater extent by slower rhythms. In addition, the amount of slow-wave activity changes during the course of a night's sleep. Thus, the method provided herein can include steps to minimise their effects. Firstly, through training, the Bayesian neural-network algorithm has the ability to generalise and recognise the characteristics of hypoglycaemic episodes against excursions of sleep stages. Secondly, the adaptive neural-network algorithm can be designed to adapt to a specific group of patients. Thirdly, the natural dynamics (average time constant) of hypoglycaemic episodes and the natural time constant related to normal excursions of sleep stages can be detected and used for positive identification of hypoglycaemia.

It will be appreciated that plasma glucose concentrations may be <2.8 mmol/L as much as 10% of the time during aggressive glycaemic therapy of Type 1 Diabetes Mellitus (DM), and an estimated 2% to 4% of people with type 1 DM die from hypoglycaemia. Furthermore, severe hypoglycaemia event rates were 115 per 100 patient-years in type 1 DM.

Importantly, hypoglycaemia and the fear of hypoglycaemia, particularly at night, severely impair a patient's quality of life. More importantly, this condition and the associated anxiety it generates can have an inhibiting effect on patients and their clinicians, discouraging patients from achieving the strict glycaemic control that otherwise could contribute substantially to preventing diabetes complications. Essentially, were it not for the potentially devastating effects of hypoglycaemia on the brain, the glycaemic management of diabetes would be rather straightforward (Cryer 2003). In addition, the system described herein can be used as a sensor for the development of an overnight artificial pancreas, which would offer substantial improvements in overall glucose control and could guarantee normoglycaemia at the start of the day.

Furthermore, it will be appreciated that the method and system described herein can provide for treatment of complications of diabetes, by focusing on an important acute complication of diabetes, hypoglycaemia. The potential beneficiaries of this device are patients with Type 1 diabetes and a percentage of approximately 180 million patients with Type 2 diabetes worldwide. The economic significance is that this monitor may gain a significant market share for diabetes glucose self-monitoring devices and a potential reduction in health care costs associated with severe hypoglycaemic events, fear of hypoglycaemia and suboptimal diabetes control.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A method for determining an indication of the presence of hypoglycaemia, the method including the steps of, in a processing system:
    a) receiving electroencephalography (EEG) signal information, including:
        (i) an alpha wave; and
        (ii) a theta wave;
    b) analysing the signal information;
    c) determining a variation from the analysis for determining an indication of the presence of hypoglycaemia, the variation including:

(i) a slowing of alpha wave activity and a shift in a centroid alpha frequency; and,
(ii) a quickening of theta wave activity and a shift in a centroid theta frequency; and,
d) determining an indication of the presence of hypoglycaemia from the variation.

2. The method of claim 1, wherein the method includes receiving signal information in a continuously moving time window.

3. The method of claim 2, wherein the method provides for a substantially real-time detection of the variation.

4. The method of claim 1, wherein the received EEG signal information further includes
a delta wave.

5. The method of claim 4, wherein analysing the signal information includes any one or a combination of:
(i) determining a shift in a centroid delta frequency;
(ii) determining a rate of change of a alpha wave frequency;
(iii) determining a rate of change of the theta wave frequency; and,
(iv) determining a rate of change in the delta wave frequency.

6. The method of claim 1, wherein the method includes receiving the EEG signal information from any one or a combination of the occipital cortex and parietal cortex.

7. The method of claim 1, wherein the method includes providing an indication of hypoglycaemia by receiving information, including an increase in delta wave activity of the EEG signal.

8. The method of claim 7, wherein the method further includes determining an average time constant of hypoglycaemic episodes and a natural time constant related to normal sleep patterns, for detecting hypoglycaemia during sleep.

9. The method of claim 1, wherein the method includes performing a data mining technique on the signal information to determine an abnormality of metabolic function and/or a variation of metabolic function.

10. The method of claim 9, wherein the method includes applying an artificial or optimised Bayesian neural network.

11. The method of claim 9, wherein the method includes training data in relation to EEG signals, associated with a particular patient.

12. The method of claim 1, wherein the method includes:
a) estimating a patient model based on an EEG response; and,
b) calculating an appropriate medicament dose for managing the variation.

13. The method of claim 12, wherein the method includes administering the dose by any one or a combination of:
a) a pump;
b) an oral device;
c) a medicament dispenser; and
d) an intravenous device.

14. The method of claim 12, wherein the method includes generating a signal to cause an automatic administration of the medicament dose.

15. The method of claim 12, wherein the variation is an indication of hypoglycaemia and the method includes calculating an appropriate glycogen/glucose dose.

16. The method of claim 1, wherein the method includes sounding an alarm when a variation is determined.

17. An artificial pancreas for managing hypoglycaemia, the artificial pancreas including:
a) a processing system, the processing system being configured to determine an indication of the presence of hypoglycaemia in accordance with the method of claim 1; and,
b) an administration device, the administration device being configured to administer an appropriate dose of glucose/glycogen to manage hypoglycaemia.

18. The artificial pancreas of claim 17, wherein the pancreas is capable of being used as an overnight device.

19. The artificial pancreas of claim 17, wherein the pancreas is at least partially implantable.

20. A system for determining an indication of the presence of hypoglycaemia, the system including a processing system, the processing system being configured to:
a) receive electroencephalography (EEG) signal information, including:
(i) an alpha wave; and
(ii) a theta wave;
b) analyse the signal information;
c) determine a variation from the analysis for determining an indication of the presence of hypoglycaemia, the variation including:
(i) a slowing of alpha wave activity and a shift in a centroid alpha frequency; and,
(ii) a quickening of theta wave activity and a shift in a centroid theta frequency; and,
d) determine an indication of the presence of hypoglycaemia from the variation.

21. The system of claim 20, wherein the processing system is adapted to receive EEG signal information from a wireless headset.

* * * * *